United States Patent [19]

Uphues et al.

[11] Patent Number: 5,281,749
[45] Date of Patent: Jan. 25, 1994

[54] PROCESS FOR REDUCING THE RESIDUAL CONTENT OF FREE ALKYLATING AGENT IN AQEOUS SOLUTIONS OF AMPHOTERIC OR ZWITTERIONIC SURFACTANTS

[75] Inventors: Guenter Uphues, Monheim; Uwe Ploog, Haan; Klaudia Bischof, Werne; Kenan Kenar, Duesseldorf; Pavel Sladek, Dueren, all of Fed. Rep. of Germany

[73] Assignee: Henkel Kommanditgesellschaft auf Aktien, Duesseldorf, Fed. Rep. of Germany

[21] Appl. No.: 859,441

[22] PCT Filed: Nov. 19, 1990

[86] PCT No.: PCT/EP90/01975

§ 371 Date: May 28, 1992

§ 102(e) Date: May 28, 1992

[87] PCT Pub. No.: WO91/08193

PCT Pub. Date: Jun. 13, 1991

[51] Int. Cl.$^5$ .............. C07C 309/14; C07C 227/14; C07C 291/00; C07C 211/03
[52] U.S. Cl. .................... 562/40; 562/400; 562/553; 562/554; 562/575; 562/576; 564/289; 564/293; 564/296

[58] Field of Search ............... 562/40, 400, 553, 554, 562/575, 56; 564/293, 289, 296

[56] References Cited

U.S. PATENT DOCUMENTS

| | | | |
|---|---|---|---|
| 3,480,665 | 11/1969 | Nagy | 562/575 |
| 3,649,677 | 3/1972 | Morris | 562/575 X |
| 3,928,447 | 12/1975 | Chen et al. | 564/296 |
| 4,359,430 | 11/1982 | Heikkala et al. | 562/575 |
| 4,453,007 | 6/1984 | Taube | 562/554 |
| 4,530,799 | 7/1985 | Hirsbruner et al. | 562/575 |

FOREIGN PATENT DOCUMENTS 56-86148  7/1981  Japan ................... 564/296

OTHER PUBLICATIONS

Starobinets et al., Chemical Abstracts, vol. 92, #93884d (1980).

Primary Examiner—Floyd D. Higel
Attorney, Agent, or Firm—Ernest G. Szoke; Wayne C. Jaeschke; Real J. Grandmaison

[57] ABSTRACT

A process for reducing the residual content of free alkylating agent in aqueous solutions of amphoteric or zwitterionic surface-active agents by aftertreatment with ammonia, an amino acid containing 2 to 8 carbon atoms, or an oligopeptide.

7 Claims, No Drawings

PROCESS FOR REDUCING THE RESIDUAL CONTENT OF FREE ALKYLATING AGENT IN AQEOUS SOLUTIONS OF AMPHOTERIC OR ZWITTERIONIC SURFACTANTS

BACKGROUND OF THE INVENTION

1. Field of the Invention

This invention relates to a process for reducing the residual content of free alkylating agent in aqueous solutions of amphoteric or zwitterionic surfactants by aftertreatment of the solutions with ammonia, an amino acid containing 2 to 8 carbon atoms or an oligopeptide.

2. discussion of Related Art

Amphoteric and zwitterionic surfactants are characterized by a molecular structure which contains two functional groups of different polarity, generally a cationic ammonium group and an anionic carboxylate or sulfonate function. Surfactants having an amphoteric or zwitterionic structure combine excellent cleaning power with good dermatological compatibility. In addition, since they form a dense stable foam in aqueous solution which does not collapse even in the presence of soap, these classes of surfactants represent valuable raw materials for the production of personal hygiene preparations, particularly hair shampoos and shower baths.

Amphoteric or zwitterionic surfactacts are synthesized from primary, secondary or tertiary amino compounds which are reacted with a suitable alkylating agent [J. Falbe (ed.), "Surfactants in Consumer Products", Springer Verlag, Berlin/Heidelberg, 1987, pages 114 et seq.].

Thus, alkyl betaines or alkyl amidobetaines of amphoteric structure are obtained, for example, from the quaternization of tertiary amines [Seifen-Öle-Fette-Wachse, 108, 373 (1982)]or fatty acid amidoamines [Parf. Kosm. Arom. 75, 67 (1968)]with halocarboxylic acids. Zwitterionic surfactants based on alkyl imidazolines which are alkylated with halocarboxylic acids [DE 36 39 752 A1] or acrylic acid [Seifen-Öle-Fette-Wachse, 109, 20 (1983)] are of particular commercial significance. By contrast, the reaction of tertiary amines with 3-chloro-2-hydroxypropane sulfonic acid to amphoteric surfactants of the sulfobetaine type, which is described for example in British patent application GB 1,541,427, is of minor importance.

All the industrial processes mentioned above have the disadvantage that the reaction of the nitrogen component with the alkylating agent is not complete so that the reaction products contain between 0.1 and 3% by weight unreacted starting materials. Since the content of free amines and unused alkylating agent has to be reduced to a low level in order to obtain toxicologically safe products of acceptable odor, there has been no shortage of attempts in the past to achieve this objective through the choice of suitable reaction conditions or by working up the reaction products.

Whereas the content of free amines in the solution of amphoteric or zwitterionic surfactants can be substantially reduced, for example, by using the alkylating agent in excess, carrying out the reaction at pH=8 to 10 [DE 29 26 479 A1], eliminating most of the amine by distillation or destroying the amine by oxidation [DE 20 63 422 A1], heating the surfactant solutions under alkaline conditions, even for several hours, only leads to a slight reduction in the residual content of alkylating agent.

Accordingly, the problem addressed by the present invention was to provide a process by which the residual content of alkylating agent in solutions of amphoteric or zwittionionic surfactants could be reduced to less than 0.01% by weight, based on a solids content of 100% by weight of the surfactant solutions.

DESCRIPTION OF THE INVENTION

Other than in the operating examples, or where otherwise indicated, al numbers expressing quantities of ingredients or reaction conditions used herein are to be understood as modified in all instances by the term "about".

The present to a process for reducing the residual content of free alkylating agent in aqueous solutions of amphoteric or zwitterionic surfactants by aftertreatment with ammonia, amino acid containing 2 to 8 carbon atoms or an oligopeptide.

By amphoteric or zwitterionic surfactants are meant product which can be obtained under alkaline conditions by alkylation of primary, secondary or tertiary amines and imidazolines with a compound from the group consisting of halocarobyxlic acids, halohydroxyalkane sulfonics acids and 1,2-unsaturated carboxylic acids and also esters thereof. Typical representatives of the nitrogen-containing component are, for example, technical grade coconut oil amine, technical grade coconut oil fatty acid amidopropyl dimethyl amine or 1-hydroxyethyl-2-undecyl imidazoline. A coconut oil alkyl group is understood to be a group which has a C chain distribution of, on average, 2% by weight $C_{10}$, 57% by weight $C_{12}$, 23% by weight $C_{14}$, 11% by weight $C_{16}$ and 7% by weight $C_{18}$.

Typical examples of the alkylating agents used are 3-chloro-2-hydroxypropane sulfonic acid, propane sultone, maleic and crotonic acid and esters thereof, but especially chloroacetic acid and acrylic acid.

The aftertreatment of the aqueous solutions of amphoteric or zwitterionic surfactants may be effected by addition of 0.2 to 10% by weight and preferably 0.5 to 3.0% by weight (based on the surfactant solution) ammonia, an amino acid containing 2 to 8 carbon atoms or an oligopeptide, preferably with heating.

Ammonia is preferably used in the form of a 25 to 55% by weight aqueous solution for the aftertreatment.

Typical examples of amino acids containing 2 to 8 carbon atoms are alanine, arginine, asparagine, cysteine, cystine, dibromotyrosine, diiodotyrosine, glutamic acid, histidine, hydroxylysine, hydroxyproline, isoleucine, leucine, lysine, methionine, phenylalanine, proline, serine, threonine, thyroxine, tryptophane, tyrosine and valine. Glycine and glutamine are preferably used.

Also suitable are oligopeptides which have a sufficiently low degree of oligomerization to be completely soluble in water under in-use conditions and in the in-use concentration. Water-soluble products of the type formed, for example, in the partial hydrolysis of proteins, for example gelatine or collagen [Angew. Chem. 90, 187 (1978)], may also be used.

The aftertreatment of the aqueous solutions of amphoteric or zwitterionic surfactants is carried out by heating the surfactant solution with the aftertreatment agent to a temperature of 50° to 100° C. and preferably to a temperature of 70° to 95° C. over a period of 0.5 to 8 h and preferably over a period of 1 to 4 h at a pH value of 7.2 to 11.5 and preferably at a pH value of 7.5 to 9.5. In general, the residual content of alkylating agent is reduced more quickly, the higher the aftertreatment temperature. The aftertreatment may also be carried out under a pressure of 1 to 2 bar and at a temperature of up to 120° C. in a pressure autoclave.

The residual content of free alkylating agent, particularly chloroacetic acid or acrylic acid, is reduced to less than 0.01% by weight (based on the solids content) in 0.5 to 8 h. Both the aftertreatment agents used and the compounds formed during the aftertreatment are toxicologically safe and do not adversely affect either the performance properties or the odor of the amphoteric or zwitterionic surfactant solutions.

The invention is illustrated by the following Examples.

EXAMPLES

Synthesis of amphoteric and zwitterionic surfactants

A. Synthesis of an amophoteric surfactant of the alkyl betaine type 130.4 g (1.1 mol) sodium chloroacetate are introduced into 679 g water in a stirred reactor equipped with a thermometer, pH electrode, dropping funnel and reflux condenser and, after the addition of 235 g (1 mol) dimethyl coconut oil amine (C chain distribution of the coconut oil alkyl function: 2% by weight $C_{10}$, 57% by weight $C_{12}$, 23% by weight $C_{14}$, 11% by weight $C_{16}$, 7% by weight $C_{18}$), are heated to 80° C. After a reaction time of approx. 2.5 h, the initially cloudy reaction mixture became clear. The pH value of the solution was kept at 8.0 to 8.5 by addition of 20% by weight sodium hydroxide solution, after which the reaction was continued until the residual content of free amine was less than 0.3% by weight. After a reaction time of 8.5 h, the reaction was terminated by cooling.

Characteristic data of the product:
Solids : 34.8% by Weight
Sodium chloride : 6.0% by weight
Free amine : 0.28% by weight=1.2 mmol/100 g
Chloroacetic acid 0.23% by weight, corresponding to 0.67% by weight, based on solids

B. Synthesis of an amphoteric surfactant of the alkyl-amidobetaine type

Example 1 was repeated using 204.4 g (1.73 mol) sodium chloroacetate in 1232 g water and 459.0 g (1.5 mol) of an amidation product of 1-aminopropyl-3-N,N-dimethyl amine and hydrogenated coconut oil fatty acid (C chain distribution; 7% by weight $C_8$, 6% by weight $C_{10}$, 49% by weight $C_{12}$, 19% by weight $C_{14}$, 9% by weight $C_{16}$, 10% by weight $C_{18}$) at a temperature of 90° C. The pH value was kept at 7.5 to 8 by addition of 20% by weight sodium hydroxide to the solution which turned clear on reaching the reaction temperature. After a reaction time of 2 hours, the reaction was terminated by cooling.

Characteristic data of the product:

Solids : 35.3% by Weight
Sodium chloride 5.2% by weight
Free amine : <0.1% by weight
Chloroacetic acid : 0.84% by weight corresponding to 2.4% by weight, corresponding to 2.4% by weight, based on solids

C. Synthesis of an amphoteric surfactants of the alkyl-amidobetaine type

Example 2 was repeated using 123.8 g (1.05 mol) sodium chloroacetate in 750 g water and 306 g (1 mol) of the amidation product.

Characteristic data of the product:
Solids : 34.5% by weight
Sodium chloride 4.8% by weight
Free amine 0.6% by weight
Chloroacetic acid 0.39% by weight, corresponding to 1.1% by weight, based on solids

D. Synthesis of a zwitterionic surfactant of the so-called imidazolinium betaine type 1,155.9 g (0.5 mol) of an imidazoline obtained from aminoethyl ethanolamine and hydrogenated coconut oil fatty acid (C chain distribution as in Example 2) and containing 11.7% by weight diamide as secondary product were introduced into a reactor corresponding to Example 1 with 6.1 g 50% by weight sodium hydroxide solution and 15.3 g water and stirred for 1 h at 90° C. in accordance with DE 30 18 201 A1. A solution of 136.3 g (1.15 mol) sodium chloroacetate in 423 g water was then added so that the temperature fell to 60° C., followed by stirring for 30 minutes. 46 g 50% by weight sodium hydroxide solution were then added to the reaction mixture, after which the solution was stirred for 3 h at 60° C. After heating to 80° C. and addition of another 46 g 50% by weight sodium hydroxide solution, the solution was stirred for 1.5 h and subsequently cooled.

Characteristic data of the product:
Solids : 39.5% by weight
Sodium chloride 7.8% by weight
Chloroacetic acid 0.57% by weight, corresponding to 1.4% by weight, based on solids

E. Synthesis of an amphoteric surfactant of the so-called salt-free alkyl amidobetaine type 1,155.9 g (0.5 mol) of an imidazoline obtained from aminoethyl ethanolamine and hydrogenated coconut oil fatty acid (C chain distribution as in Example 2) and containing 11.7% by weight diamide as secondary product were dissolved in 284.4 g water. 36.5 g (0.51 mol) acrylic acid were added dropwise to the mixture over a period of 0.5 h at 50° to 60° C. The mixture was then stirred for 5 h at 90° C. and subsequently cooled.

Characteristic data of the product:
Solids : 41.6% by weight
Acrylic acid : 1.8% by weight, based on solids.

To determine the solids content, the surfactant solutions were dried for 2 h at 110° C. in a drying cabinet and the water loss which was complete under these conditions was determined by differential weighing.

To determine the content of free amine, the solution was first adjusted to pH 3.0 with hydrochloric acid and the amine hydrochloride formed was potentiometrically titrated with sodium hydroxide solution.

The content of chloroacetic acid and acrylic acid was determined by ion chromatography using an ion exchanger column. Detection was carried out with a conductivity detector after a suppressor reaction. Identification was based on the retention times of the components; quantitative evaluation was carried out by comparison with calibration standards through integration of the peak areas.

EXAMPLES 1 to 10

Aftertreatment of the amphoteric and zwitterionic surfactants

Quantities of 200 g of the products obtained in accordance with A, B, C, D and E were aftertreated with and without 0.5 to 1.8% by weight (based on 100% by weight surfactant solution) ammonia (25% by weight), an amino acid containing 2 to 8 carbon atoms or an oligopeptide at 90° C. and at a pH value of 8.5 to 9.0. The content of chloroacetic acid and acrylic acid was determined by ion chromatography at intervals of 1 h. The results are set out in Tables 1 and 2.

TABLE 1

Aftertreatment of the amphoteric and zwitterionic surfactants. All figures relating to the chloroacetic acid content were based on a solids content of the solutions of 100% by weight

| Ex. | Amphoteric surfactant | Aftertreatment component % by weight | Chloroacetic acid content after | | | |
|---|---|---|---|---|---|---|
| | | | 1 h | 2 h | 3 h | 4 h |
| | | | $10^{-4}$ % by weight | | | |
| | A | None | 5700 | 5400 | 5200 | 4900 |
| 1 | A | 0.5% glycine | 3700 | 2400 | 170 | 90 |
| 2 | A | 1.0% glycine | 2400 | 900 | 100 | 50 |
| | B | None | 20000 | 19000 | 17000 | 14000 |
| 3 | B | 0.5% glycine | 2000 | 60 | 60 | 30 |
| 4 | B | 1.0% glutamine | 5900 | 2600 | 700 | 100 |
| 5 | B | 1.0% NH$_3$ sol.* | 3700 | 60 | 60 | 30 |
| | C | None | 5800 | 4400 | 3800 | 2500 |
| 6 | C | 0.5% glycine | 290 | 60 | 30 | 0 |
| | D | None | 13000 | 11000 | 10000 | 9000 |
| 7 | D | 1.0% glycine | 1260 | 25 | 0 | 0 |
| 8 | D | 1.8% glutamine | 3200 | 1500 | 500 | 25 |
| 9 | D | 2.0% NH$_3$ sol.* | 2600 | 130 | 25 | 0 |

*NH$_3$ solution, 25% by weight

TABLE 2

Aftertreatment of the amphoteric and zwitterionic surfactants. All figures relating to the acrylic acid content were based on a solids content of the solutions of 100% by weight

| Ex. | Amphoteric surfactant | Aftertreatment component % by weight | Chloroacetic acid content after | | | |
|---|---|---|---|---|---|---|
| | | | 1 h | 2 h | 3 h | 4 h |
| | | | $10^{-4}$ % by weight | | | |
| | E | None | 17200 | 17000 | 17000 | 16800 |
| 10 | E | 0.5% glycine | 2300 | 950 | 320 | 90 |

We claim:

1. The process of reducing the residual consent of free alkylating agent in an aqueous solution of amphoteric or zwitterionic surfactant, comprising adding to said solution from about 0.2 to about 10% by weight, based on the weight of said solution, of a treatment agent selected from the group consisting of ammonia, an amino acid containing 2 to 8 carbon atoms, and an oligopeptide, and heating said solution to a temperature of from about 50° C. to about 100° C. for about 0.5 to about 8 hours at a pH value of from about 7.2 to about 11.5.

2. A process as in claim 1 wherein said treatment gent is present in the amount of from about 0.5 to about 3% by weight, based on the weight of said solution.

3. A process as in claim 1 wherein said amino acid is selected from glycine and glutamine.

4. A process as in claim 1 including heating said solution to a temperature of from about 70° C. to about 95° C. for about 1 to about 4 hours at a pH value of from about 7.5 to about 9.5.

5. A process as in claim 1 including heating said solution to a temperature of up to about 120° C. and under a pressure of about 1 to about 2 bar.

6. A process as in claim 1 wherein said alkylating gent is selected from chloroacetic acid and acrylic acid.

7. A process as in claim 6 wherein the residual content of said free alkylating agent is reduced to less than about 0.01% by weight, based on the solids content of said solution.

* * * * *